March 28, 1972 R. S. MOORE Plant Pat. 3,083
MINIATURE ROSE PLANT
Filed Jan. 28, 1970
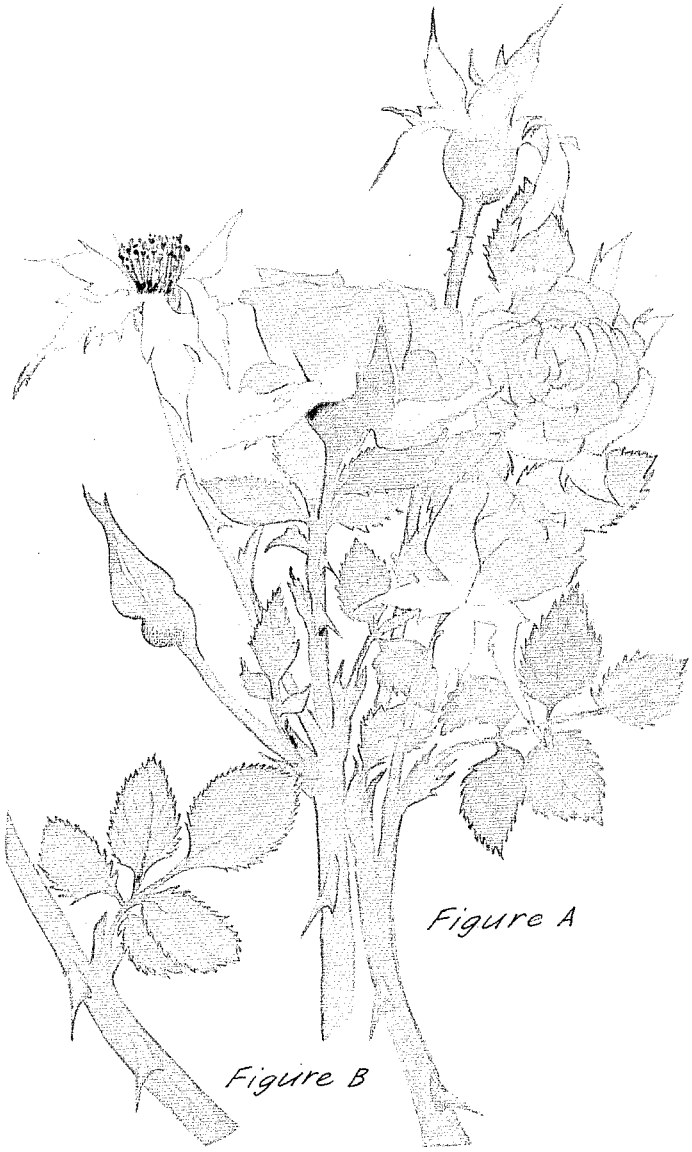
WITNESS
Jeanette Nunn Copley
INVENTOR
Ralph S. Moore

United States Patent Office

Plant Pat. 3,083
Patented Mar. 28, 1972

3,083

MINIATURE ROSE PLANT

Ralph S. Moore, 2519 E. Noble Ave.,
Visalia, Calif. 93277

Filed Jan. 28, 1970, Ser. No. 6,604
Int. Cl. A01h *5/00*
U.S. Cl. Plt.—10 1 Claim The present invention relates to a new and distinct variety of hardy, relatively dwarf, bush type rose of the hybrid miniature class; the variety being primarily characterized—as to novelty—by bright orange red buds and flowers which in general color effect are all over orange red color (with a somewhat fluorescent sheen) from the opening bud stage to the finished flower.

The variety is further characterized by:

An abundance of bloom, with flowers borne usually in loose clusters (sometimes singly on young plants).

Little or no fragrance.

A plant which is vigorous, of bushy upright shape, and with dark green, glossy, medium small, mildew resistant foliage with pointed leaflets; the bud and flower being similar in size and form to the miniature rose (Cricri (not patented) but of a shade of orange red color similar to miniature rose Starina (U.S. Plant Pat. No. 2,646) and borne on somewhat stiffer stem. The plant which has a normal average height of 14 to 18″ at maturity can easily be maintained at a lower height with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Baccara (U.S. Plant Pat. No. 1,367), a greenhouse variety, as the seed parent, and miniature rose Eleanor (U.S. Plant Pat. No. 2,175) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, relatively dwarf; bush; seedling; greenhouse; outdoors; cut flowers; garden decoration; potted plant.

Class: Miniature

Flowers:

*Continuity.*—Intermittent to continuous throughout season.

*Fragrance.*—Little or none.

*Lasting quality.*—Better than average.

Flowers borne: Usually in loose clusters, several together, on medium length quite stiff (wire-like) stems.

Quantity of bloom: Average to above average both outside and in greenhouse.

Bud:

*Peduncle.*—Long; slender; wire-like; erect; medium to deep green; nearly smooth with occasional tiny reddish prickles.

*Before calyx breaks.*—Size—Small.

*Form.*—Short pointed; with foliaceous appendages on surface of bud and foliaceous parts extending beyond the tip of the bud equal to less than one half of its length.

*Color.*—Medium green (in greenhouse) with sometimes a bronzy tint. As calyx breaks; color red; size—small.

*Form.*—Medium length; short-pointed.

*Opening.*—Opens well in all weather.

Bloom:

*Size when fully open.*—Small averaging about 1½″.

*Petalage.*—Double—30 to 40 petals arranged regularly.

*Form.*—Flat or slightly cupped at first; later maturity remaining relatively flat or cupshaped with a few of outer petals rolled slightly outward.

Petals: Rather thick; stiff; satiny both inside and outside.

*Shape.*—Outside petals broad lanceolate (often nearly round) with small acute tip; intermediate—broad lanceolate with acute tip; inside lanceolate with acute tip.

Color: Newly opened flower from plant grown in plastic house (November 1969), Visalia, Calif.

Outside petal: Outside surface—Carmine 21 (sometimes with darker shadings) blending to near white at base; inside surface—Geranium Lake 20 (sometimes with darker shadings) shading to near white at base.

Intermediate petal: Outside surface—Carmine 21 (sometimes with darker shadings) blending to near white at base; inside surface—Geranium Lake—shading to near white at base.

Inside petal: Outside surface—same as intermediate petal; inside surface—same as intermediate petal.

General color effect newly opened: Uniform bright orange red.

Three days open: Essentially same orange red color.

Behaviour: Spent blooms persist for short time then petals drop clean.

Flower longevity:

*(Fall 1969) in greenhouse.*—6 to 10 days or longer.

*Outdoors (fall 1969).*—6 to 10 days.

*Cut flowers at living room temperature.*—4 to 6 days or longer.

Reproductive organs:

*Stamens.*—Numerous; arranged regularly about pistil.

*Filments.*—Short, yellow.

*Anthers.*—Well formed, yellow.

*Pollen.*—Moderately abundant, yellow.

*Pistils.*—Abundant.

*Styles.*—Short to very short, bunched, near white.

*Stigma.*—Near white.

*Ovaries.*—All enclosed in calyx.

*Hips.*—Few, round, orange red when ripe.

*Sepals.*—Permanent; spear shaped.

*Seeds.*—Very few—usually but 1 or 2 per hip.

Foliage:

*Leaves.*—Compound of five leaflets (occasionally 3); abundant; medium small; leathery; glossy.

*Leaflets.*—Shape: lanceolate, nearly oval; apex acute; base rounded; margin serrate. Color: medium to dark green; new growth sometimes tinted bronze (outdoors). Rachis: strong; upper side grooved with a few small, nearly straight, thorns or prickles; under side sparsely thorny.

*Stipules.*—Medium long; relatively broad; short points, turning out at an angle of about 45 degrees.

Growth:

*Habit.*—Bushy; upright; much branched.

*Growth.*—Strong; vigorous.

*Canes.*—Medium to strong.

*Main stems.*—Color: medium green (indoors); green to bronzy or reddish outdoors. Thorns: moderately thorny; slender; medium length; hooked slightly downward with sharp points; color—light to medium brown. Some prickles. Hairs.—none.

*Branches.*—Color: medium green. Thorns: moderately thorny; medium length; hooked slightly downward; sharp points; medium length narrow oval base. Prickles—few or none.

*Hairs.*—None.

*New shoots.*—Color: medium green (often tinted bronze outdoors). Thorns: moderately thorny; medium length; hooked slightly downward; sharp points; base oval; color—green to reddish brown. Prickles—none. Hairs—none.

The minature rose plant and its flowers as herein described may vary in slight detail due to climatic, soil and cultural conditions under which the variety may be grown; the present description being of the variety as grown at Visalia, Calif.

The following is claimed:

1. A new and distinct variety of hybrid miniature rose plant of hardy, moderately dwarf, much branched, upright, bush type, as illustrated and described, characterized by resemblance to the Cricri miniature rose (not patented) in general form of bud and flower (with less petals) but more nearly resembling Starina miniature rose (U.S. Plant Pat. No. 2,646) in color, the general color effect of the freshly opened flower being an all over orange red color of uniform shade with little tendency to fade, the flowers having extremely long lasting quality both on the plant and as cut flowers; and further characterized by a plant which is moderately dwarf, much branched and vigorous in growth, easy to propagate from cuttings and by buding; with medium small, dark green mildew resistant foliage, an abundance of bloom borne in repeated succession throughout the growing season with flowers borne usually in loose clusters on stiff wiry stems.

No references cited.

ROBERT E. BAGWILL, Primary Examiner